United States Patent [19]
Feldon et al.

[11] Patent Number: 4,747,296
[45] Date of Patent: May 31, 1988

[54] ELECTRONIC TONOMETER WITH BASELINE NULLING SYSTEM

[75] Inventors: Steven E. Feldon, San Marino; David A. Wallace, Beverly Hills; Gary Mezack, Norco; Robert A. Monsour, Pasadena, all of Calif.

[73] Assignee: Design Team Partners, Glendale, Calif.

[21] Appl. No.: 781,240

[22] Filed: Sep. 27, 1985

[51] Int. Cl.$^4$ .............................................. G01L 27/00
[52] U.S. Cl. ..................................... 73/4 R; 73/753; 128/652; 324/130; 330/9; 364/558
[58] Field of Search ............... 128/645, 646, 647, 648, 128/649, 650, 651, 652; 73/4 R, 4 V, 4 D, 701, 753, 1 B, 726, 708; 324/130; 364/558, 571; 330/9; 340/347 CC

[56] References Cited

U.S. PATENT DOCUMENTS

| | | | |
|---|---|---|---|
| 3,266,288 | 8/1966 | Andresen, Jr. et al. | 73/4 R |
| 3,366,948 | 1/1968 | Price | 340/347 CC |
| 3,475,600 | 10/1969 | Spence | 324/130 UX |
| 3,641,444 | 2/1972 | Watts | 364/571 X |
| 3,748,587 | 7/1973 | Aumiaux | 330/9 |
| 3,781,869 | 12/1973 | Sudnick et al. | 364/571 X |
| 3,810,031 | 5/1974 | Poujois | 330/9 |
| 3,884,079 | 5/1975 | Turtle et al. | 73/701 |
| 3,889,518 | 6/1975 | Denouter et al. | 73/4 R |
| 3,924,612 | 12/1975 | Dempster et al. | 73/4 R X |
| 3,926,056 | 12/1975 | Brown | 73/753 |
| 4,003,370 | 1/1977 | Emil et al. | 73/753 X |
| 4,086,804 | 5/1978 | Ruby | 73/4 R |
| 4,088,009 | 5/1978 | Fukuda | 73/4 R |
| 4,263,918 | 4/1981 | Swearingen et al. | 128/681 |
| 4,322,977 | 4/1982 | Sell et al. | 73/701 |
| 4,532,809 | 8/1985 | Antonazzi et al. | 73/701 |

FOREIGN PATENT DOCUMENTS

| | | | |
|---|---|---|---|
| 1549197 | 12/1968 | France | 330/9 |
| 36077 | 3/1977 | Japan | 73/4 R |
| 44943 | 3/1980 | Japan | 73/708 |
| 135724 | 10/1980 | Japan | 73/701 |

OTHER PUBLICATIONS

"Carrier Amplifier Has Zero Drift"; *Electronics*, vol. 25, No. 12, pp. 131-133; Dec. 1952; Angelo Perone.

*Primary Examiner*—Tom Noland
*Attorney, Agent, or Firm*—Lyon & Lyon

[57] ABSTRACT

Disclosed is a battery powered, hand-held self-contained electronic tonometer with a digital readout for displaying pressure in millimeters of mercury. The tonometer includes a transducer which is a solid state pressure sensitive element and which produces a voltage proportional to intraocular pressure. An electrical waveform is produced by gently bringing the transducer in contact with the cornea. The waveform is converted to a digital signal and processed by a single chip microprocessor. The baseline of a reference signal is nulled by equalizing the charges on two capacitors on the inputs of two differential amplifiers. Equalizing the differential inputs of the two amplifier stages results in a gain of zero and removes any carrier signal. Microprocessor software detects the baseline condition established by equalizing the differential inputs. The microprocessor then looks for a series of valid measurements and calculates the average intraocular pressure along with an estimate of reliability. This average value and the reliability indicator are displayed on a liquid crystal display.

4 Claims, 7 Drawing Sheets

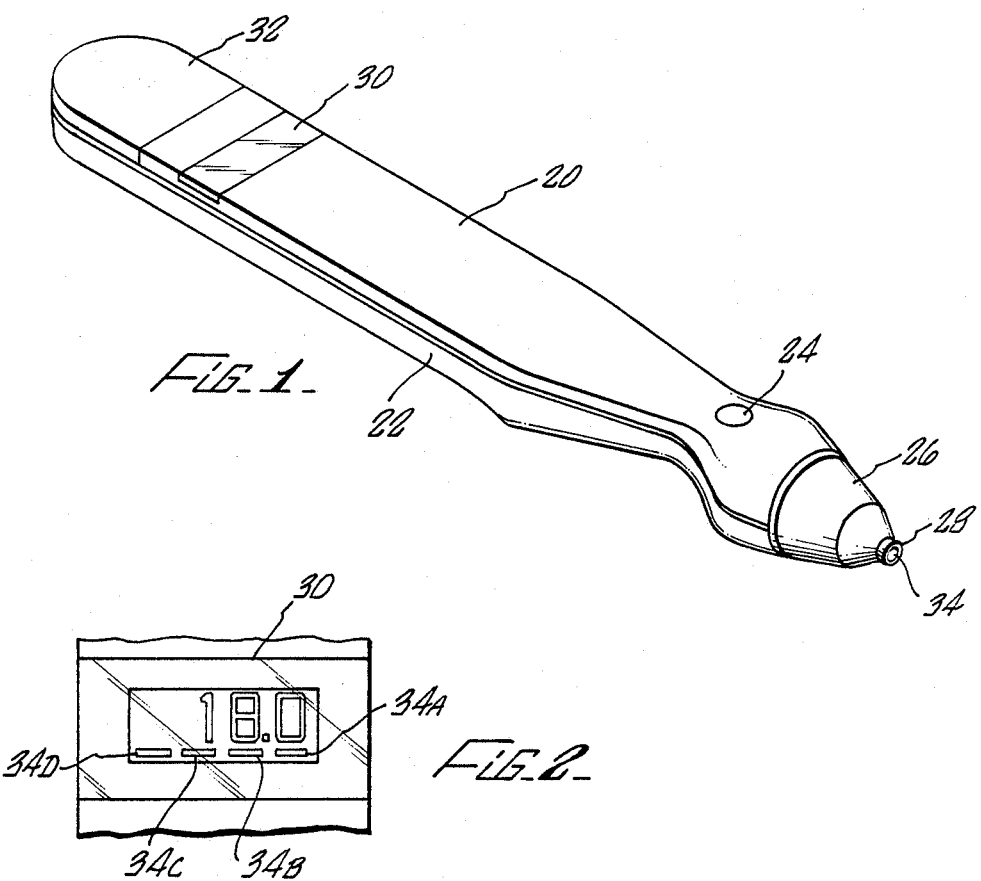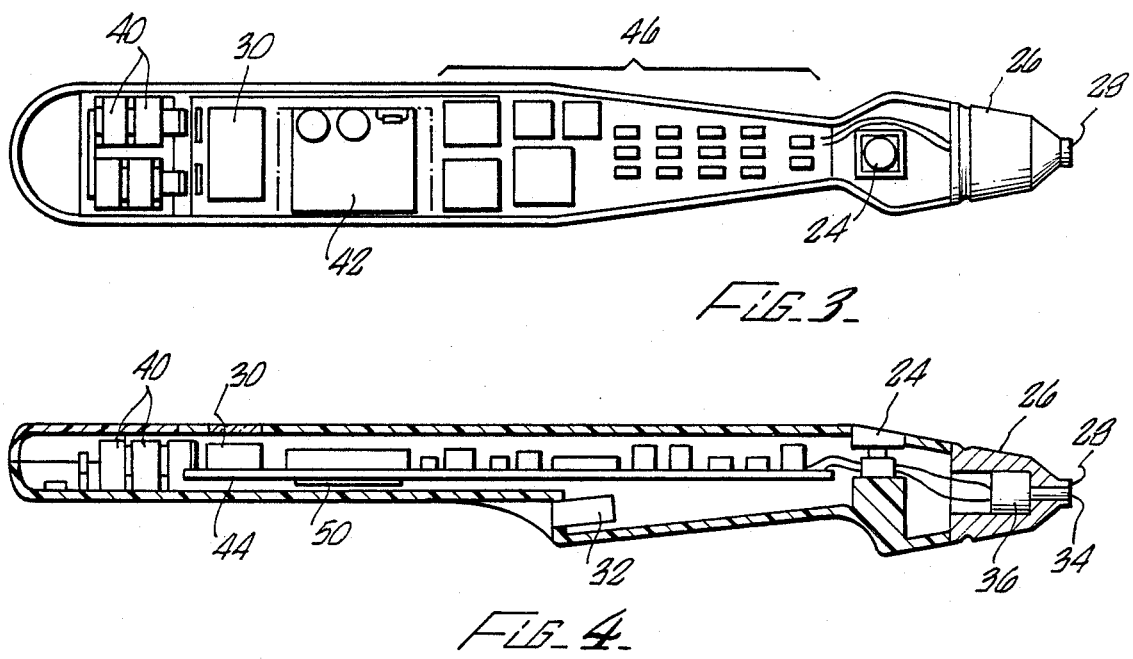

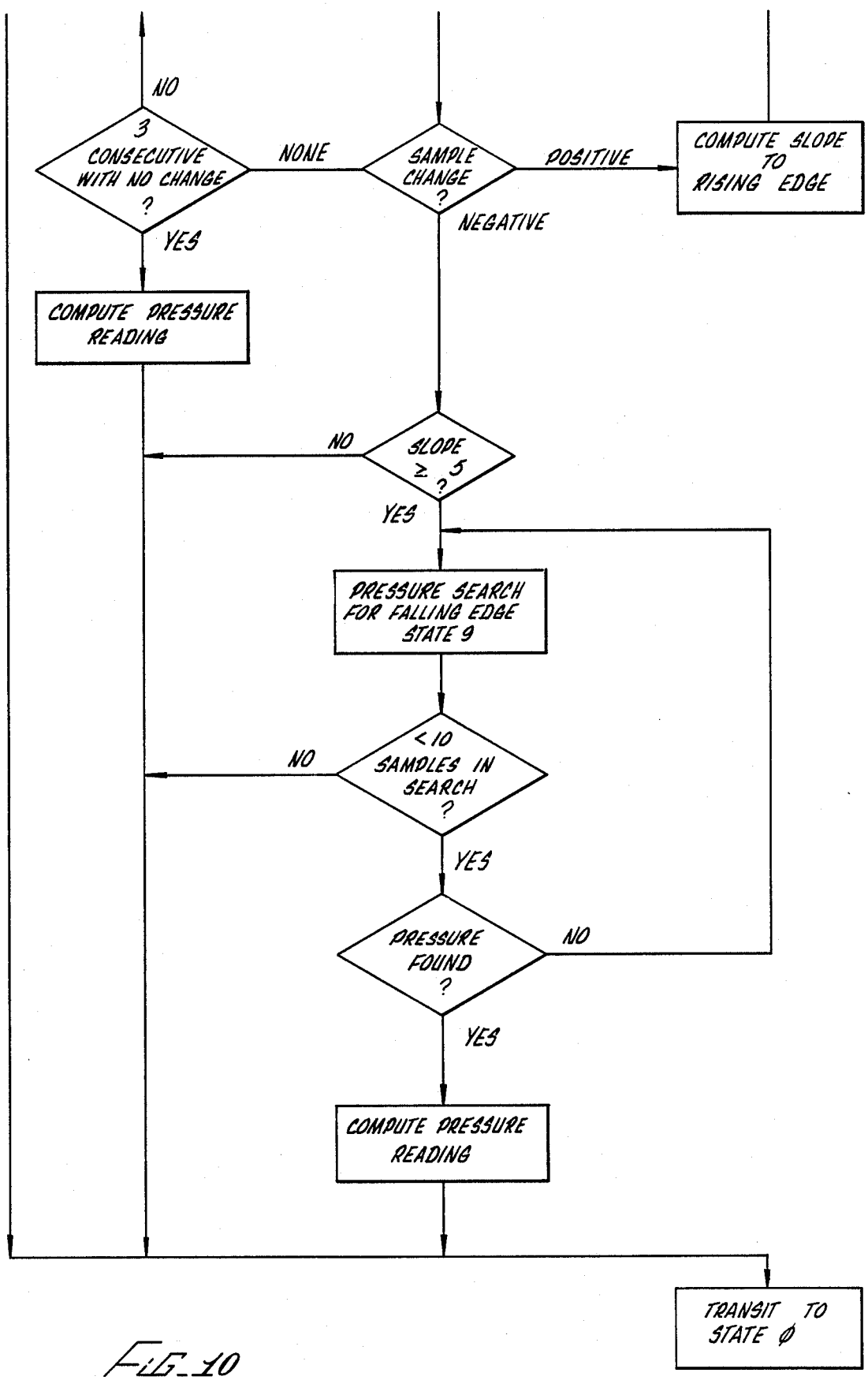
FIG_10

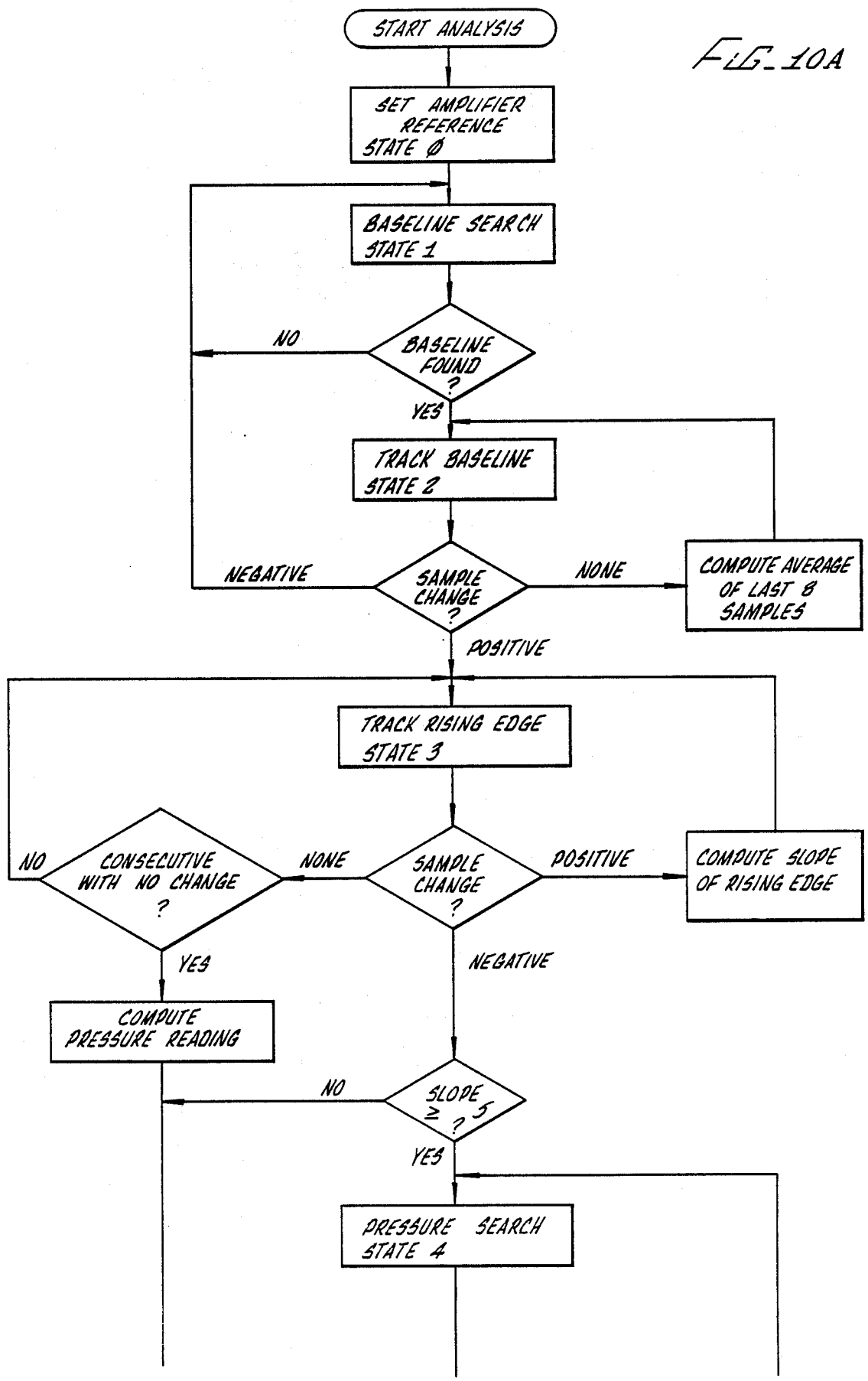
FIG_10A

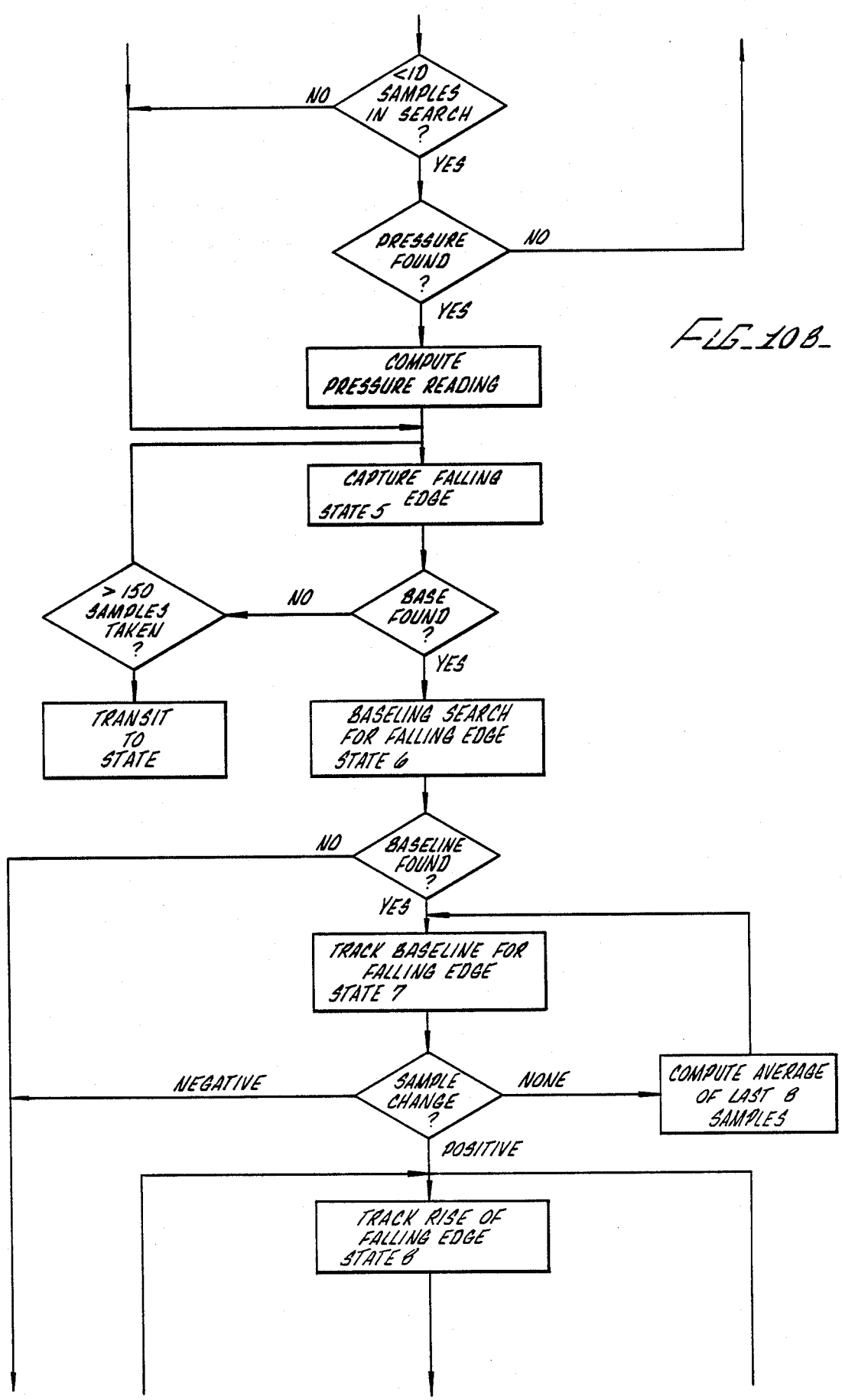
FIG_10B

ELECTRONIC TONOMETER WITH BASELINE NULLING SYSTEM

BACKGROUND OF THE INVENTION

The measurement of intraocular pressure is an important function performed by ophthalmologists and other eye care professionals. Pressure measurements are performed (a) as a routine part of the complete eye examination to identify patients with or at risk for developing glaucoma, (b) to monitor progress and response to treatment in patients with glaucoma and ocular hypertension.

The first tonometer was developed in 1926 and is called the Schiotz tonometer. This simple instrument employs a weighted plunger which is lowered onto an anesthetized eye. The amount of deflection of an indicator is proportional to intraocular pressure; however it is also sensitive to scleral rigidity which could lead to an inaccurate measurement. The intraocular pressure is obtained indirectly using a supplementary table. This somewhat difficult-to-use and inaccurate instrument is still popular today among older eye physicians and in general medical practice.

The Goldman applanation tonometer was developed in 1957 to measure intraocular pressure using an applanation method. The anesthetized cornea is flattened against a glass plate of known diameter, producing a meniscus of tear film between the head of the instrument and the cornea. This technique is less sensitive to scleral rigidity. However, the Goldman tonometer must be attached to a slit-lamp microscope so that the manual measurement can be made accurately.

There is a portable version of the Goldman tonometer known as the Perkins tonometer which is a hand held device employing similar applanation technology. However, this instrument is quite difficult to use as the examiner's eye must be literally within inches of the patient's eye and stabilization of the instrument is difficult. Therefore, except for examinations under anesthesia, the Perkins tonometer is rarely used.

The McKay/Marg tonometer, introduced in 1959, exploits different technology. This instrument incorporates a small electrical strain gauge in the tip of the hand-held probe which is attached to a large carrying case containing an amplifier, strip chart recorder, and transformer. This is a contact device and therefore requires the use of topical anesthesia. The instrument works by relating a change in voltage to intraocular pressure. The user interprets the strip chart output signal, usually interpolating over several subjectively "acceptable" signals.

The Pneumotonometer was introduced in 1975. It works by bringing a small air burst toward the cornea. The back pressure is sensed, and is found to be proportional to intraocular pressure. This instrument seems to have inaccuracies, especially at the low range.

Another instrument by A. O. Reichert utilizes an air applanation technique, which does not require touching the instrument to the eye. An air puff of a given force and diameter is used to flatten the cornea. The amount of flattening is sensed by the machine and is proportional to pressure. This is the most popular unit in the optometric community because it does not require topical anesthesia.

Harold Rose and Bruce Sand developed an applanation tonometer which utilizes a digital read-out and is described in U.S. Pat. No. 3,724,263.

Although some of the above instruments provide reliable estimates of intraocular pressure, they lack portability, reliability, accuracy, or acceptance in the marketplace, and none of the instruments are ideal in providing some key features. Therefore, eye care professionals and the general medical community is still seeking a precise hand held portable tonometer to assist them in the diagnosis and management of glaucoma.

CROSS REFERENCE TO RELATED APPLICATIONS

The present invention is related to the apparatus disclosed in the application entitled "Digital Ultrasonic Instrument for Ophthalmic Use" filed concurrently herewith in the names of David A. Wallace M.D., Steven E. Feldon M.D., Gary P. Mezack, Douglas L. Whiting Ph.D., William J. Dally and Scott A. Karns with Ser. No. 781,257 and incorporated herein by reference. The present invention is also related to the apparatus disclosed in the application entitled "Self-Contained Hand-Held Ultrasonic Instrument for Ophthalmic Use" filed concurrently herewith in the names of Steven E. Feldon M.D. and David A. Wallace M.D., with Ser. No. 781,148 and incorporated herein by reference.

SUMMARY OF THE INVENTION

The electronic tonometer is comprised of a precision strain gauge, a three stage high gain amplifier, and a microprocessor. The microprocessor is highly interactive with the amplifier circuitry to insure accurate data acquisition and control. The differential output of the strain gauge is fed into a first stage amplifier where it is converted to a single-ended non-differential output. A modulated carrier signal is successively amplified by the second and third stages of the amplifier circuitry and processed by an internal analog-to-digital (A/D) converter in a Hitachi 6305 microprocessor. While the microprocessor is in the data analysis mode, it enters as many as ten states of logical processing to acquire and process the carrier signal. The microprocessor only requires the differential levels of this signal for accurate processing and does not require absolute voltage reference levels. It is necessary that the second and third stages of the amplifiers be nulled before the measurement and analysis process can begin. This involves finding a stable amplifier baseline to reference and calculate the relative amplitude of the pressure waveform. To accomplish this, the microprocessor applies an active high capacitor discharge signal for a period of 60 mS. This nulls both the second and third stages of the amplifier circuitry by equalizing the charge on the inputs to the second and third stage amplifiers. This neutralizing effect equalizes both differential inputs for each amplifier stage, resulting in a gain of zero and removing any carrier signal. This process allows the microprocessor to reset the baseline when needed while dynamically processing the pressure waveform. The amplifiers are effectively dc coupled (since there is virtually an infinite time constant) which gives the microprocessor a dc level signal to process. In a conventional ac coupled amplifier circuit, nulling would have to be accomplished either by a complex precision auto/nulling hardware circuit or by operator manual calibration before instrument use.

Therefore it is an object of the present invention to provide the eye care professionals and general medical community with a precise self-contained hand-held portable tonometer that is reliable and accurate so as to assist them in the diagnosis and management of ocular hypertension and glaucoma.

BRIEF DESCRIPTION OF THE DRAWINGS

FIG. 2 is a front view of the liquid crystal display.

FIG. 3 is a top view of the tonometer showing the placement of the various components inside the instrument.

FIG. 4 is a section view of the tonometer showing component placement.

FIG. 7 is a circuit diagram of the three-stage amplifier with its associated baseline reference nulling circuit.

FIG. 10A through 10C are flow diagrams of a program.

DETAILED DESCRIPTION OF THE PREFERRED EMBODIMENT

The tonometer consists of a housing that is contoured such that it is easily grasped, in a manner of a writing pen. The tip of the instrument is the solid state pressured transducer element. The other functioning components of the instrument include an activation button, located on the anterior dorsel surface in close approximation to the index fingertip of the user, a liquid crystal display, a reset button, and a removable battery cover.

The measurement transducer is a solid phase pressure sensitive element which produces a change in voltage with a change in intraocular pressure. The electrical waveform produced by gently bringing the transducer in contact with the cornea is converted to a digital signal and processed by a microprocessor. The microprocessor is highly interactive with the amplifier circuitry, insuring accurate data acquisition and control. The microprocessor uses multiple criteria such as slope and configuration of the waveform for accepting a reading as valid and then calculates the average intraocular pressure along with an estimate of its reliability. An average pressure value and the reliability are then read out on a liquid crystal display.

Figure 1:
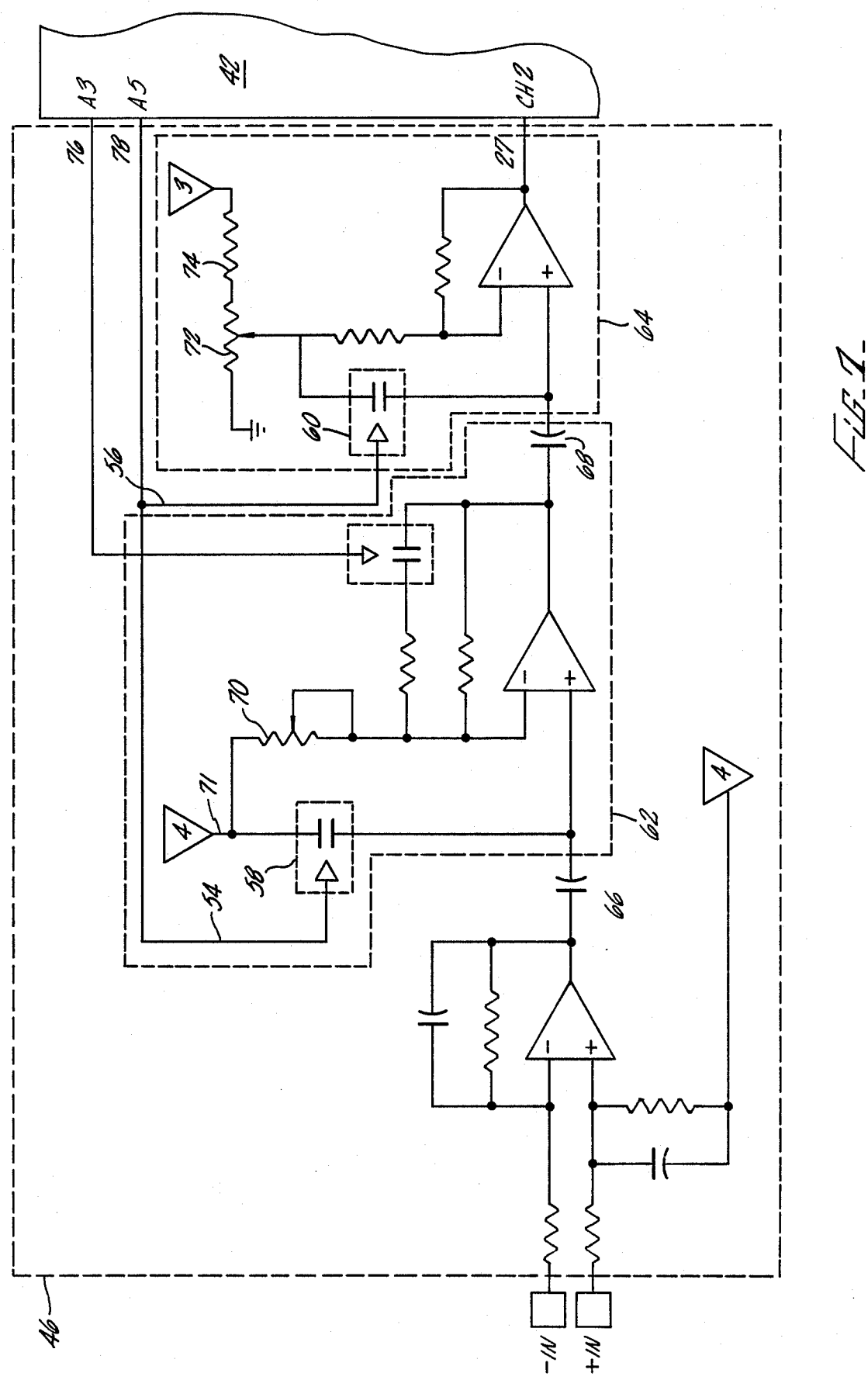
FIG. 1 is a perspective drawing of the tonometer.

FIG. 1 shows a perspective view of the tonometer 20. The tonometer 20 has a housing 22 which is formed so that a user can grasp the instrument and have his or her index finger over activation switch 24. The transducer housing 26, contains a strain gauge that is used to convert the pressure indications from the cornea to electrical impulses. The contact head 28 of the transducer housing 26 has a thin rubber membrane which covers a central post 34 (FIG. 4) attached to the strain gauge 36. After repeated measures are obtained by intermittent contact with the cornea, the pressure is then read out on the liquid crystal display 30 shown in FIG. 2.

FIG. 3 is a top view of the tonometer 20 with its various components. The batteries 40 are located toward the rear of the tonometer. Adjacent to the batteries 40 is the display 30 and adjacent to the display 30 is a microprocessor 42. A three-stage high-gain amplifier 46 and its baseline reference nulling circuit are located forward of the microprocessor on a printed circuit board 44 (FIG. 4). The activation button 24 is located on the top forward portion of the instrument for easy operation by the user.

Figure 9A:
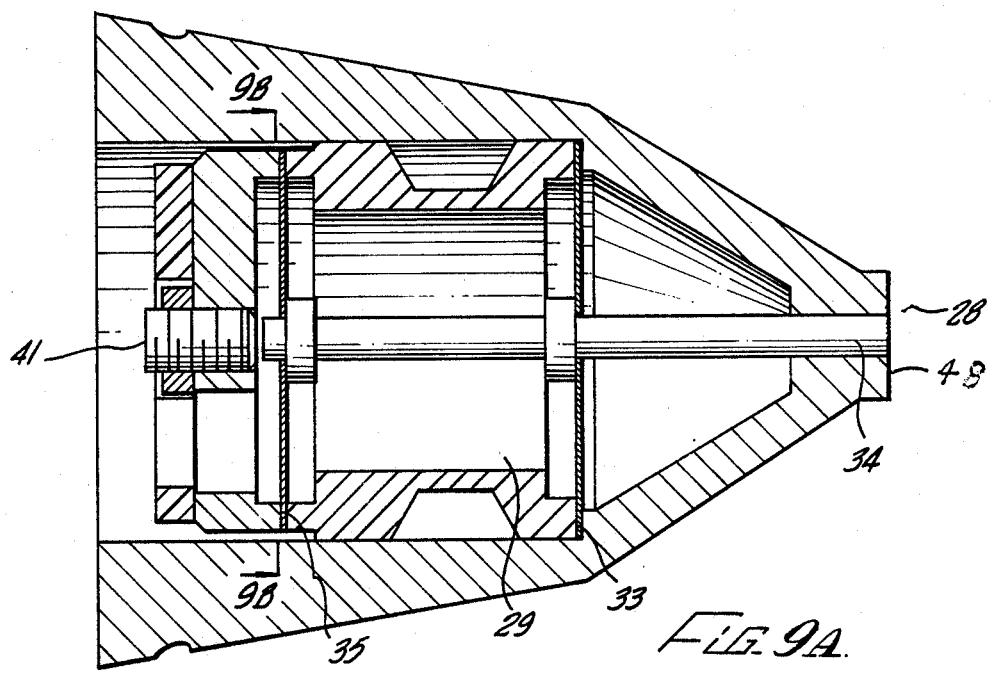
FIG. 9A is a section view of the pressure transducer and FIG. 9B is a top view of strain gauges on a plate which is shown in position in FIG. 9A by arrows 9B.
Figure 9B:
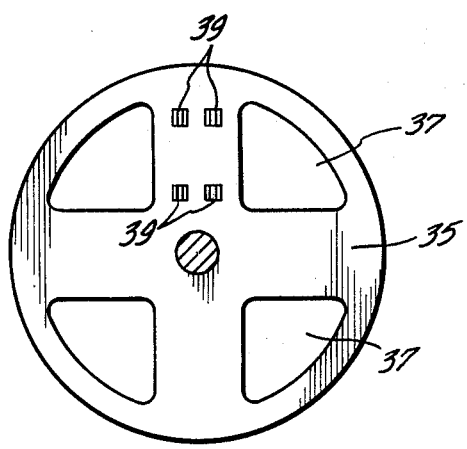

In FIG. 9A, the transducer comprises a contact head 28 and an internal assembly 29. The contact head 28 contains two components, a base 48 and a central post 34. The central post 34 is flush with the base 48, but may vary up to 0.5 microns from the base 48 without affecting the measurement. The central post 34 is welded to two flexures 33 and 35 which are 0.002 of an inch thick and one half inch in diameter. Multiple cutouts 37 are shown which serve to decrease mass while preserving strength of the elements. The anterior flexure 33 is passive, serving primarily to align the posts. The posterior flexure 35 is active in the measurement in intraocular pressure. Mounted on the flexure are four miniature impedance-matched solid state sensors 39, two of which are configured to be altered by stress and two by strain. The circuitry is configured as a Wheatstone bridge. Balancing resistors and thermal correction resistors are added to the circuit, as required. A voltage of two to six volts is utilized to activate the bridge when pressure is applied to the central post 34. This force causes a change in the flexure state which is proportional to an output voltage. A stop 41 is placed posterior to the active flexure in order to protect against accidental long excursions of the post.

The central post has a mass which produces a measurable force when the transducer is moved from a "tip down" to a "tip up" position. The calibration mode is initiated by two presses of the activation button 24 in rapid succession. There is an automatic calibration of the electrical output of the transducer to an interval value representing the force supplied by gravity on the mass of the central post 34. If the discrepancy between stored and calibrated values differ by 10%, the instrument cannot be put into the measurement mode. Recalibration, however, can be attempted.

Figure 6:
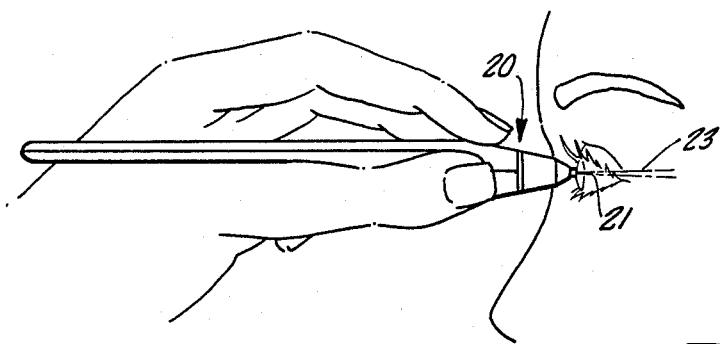
FIG. 6 is a perspective drawing of the instrument as used to make a pressure reading on a patient's eye.

The transducer must be aligned perpendicularly to the corneal surface as shown in FIG. 6 wherein the tonometer 20 is shown aligned with the visual axis 23 of the eye 21. Incomplete or off-axis contact results in slow and/or inadequate excursion of the post. When a correct applanation of the tonometer onto the eye is made, a sharply rising edge of the electrical waveform is elicited from the transducer shown as edge 90 in FIG. 8. Continuing pressure beyond that necessary to contact the cornea results in an artificial elevation of intraocular pressure by the instrument itself, shown in FIG. 8 as peak 93. At the point of optimal contact, there is a minimal indentation of the cornea by the base of the transducer tip. This results in a small transient depression 92 of voltage which best correlates with intraocular pressure as determined by manometric techniques.

Figure 8:
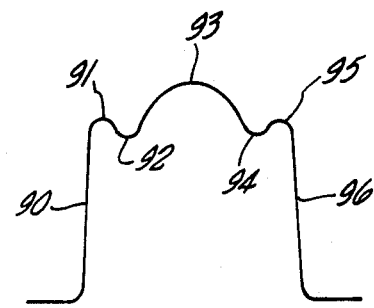
FIG. 8 is a waveform resulting from a pressure measurement.

As the transducer is removed from the cornea, a mirror image of the applanation waveform is produced such that the case of minimal corneal indentation is again achieved with a second corresponding minimum 94 in an otherwise stable voltage, following which the voltage rapidly returns to baseline as shown by falling edge 96. This waveform is shown in FIG. 8. Thus, voltage depression 92 and voltage depression 94 are substantially equivalent and best correlate with intraocular pressure.

The output voltage of the transducer 36 is ac coupled. To prevent a wandering baseline between measurements, a capacitor is shorted just prior to activating the transducer. The analog electrical signal is then digitized by the microprocessor 42 at a sampling rate of 200 to 300 Hz. Up to 32 sequential values are stored in random access memory in the microprocessor 42 and analyzed.

Analysis begins upon momentary application of the contact head 28 to the eye and consists of determining criteria for the baseline, for perpendicular application and release of the transducer to/from the cornea, and for optimal indentation. With each readable momentary application of the contact head 28 to the eye, a brief click is heard by the user, supplied by the microspeaker 50, and which is elicited by a train of electrical signals delivered from the microprocessor 42 to the microspeaker 50 mounted on the printed circuit board. All readable measures of intraocular pressure are averaged after six measurements are obtained. The range is then computed. A "beep" is given by means of a medium frequency output from the microprocessor 42 to the microspeaker 50, signaling that a reading has been obtained. The mean intraocular pressure in millimeters of mercury (Hg) is then shown on the liquid crystal display 30. One or more of four annunciator bars 34A, 34B, 34C and 34D may be illuminated denoting a correlation variance which is plus or minus 5% of the mean, shown by annunciator 34A, plus or minus 10% of the mean, shown by annunciator 34B, plus or minus 20% of the mean, shown by annunciator 34C, and greater than plus or minus 20% of the mean, shown by annunciator 34D. If ten applications of the transducer are made without achieving six readable measurements, no numeric value is displayed and the "beep" is given. The annunciator bars are shown in FIG. 2 in relationship to the display 30. At any new touch of the activation button, the microprocessor allows new measurements of intraocular pressure to be obtained. FIG. 6 shows the tonometer 20 being used to make a pressure measurement on a patient's eye 21 along the visual axis as shown by dotted line 23.

Figure 5:
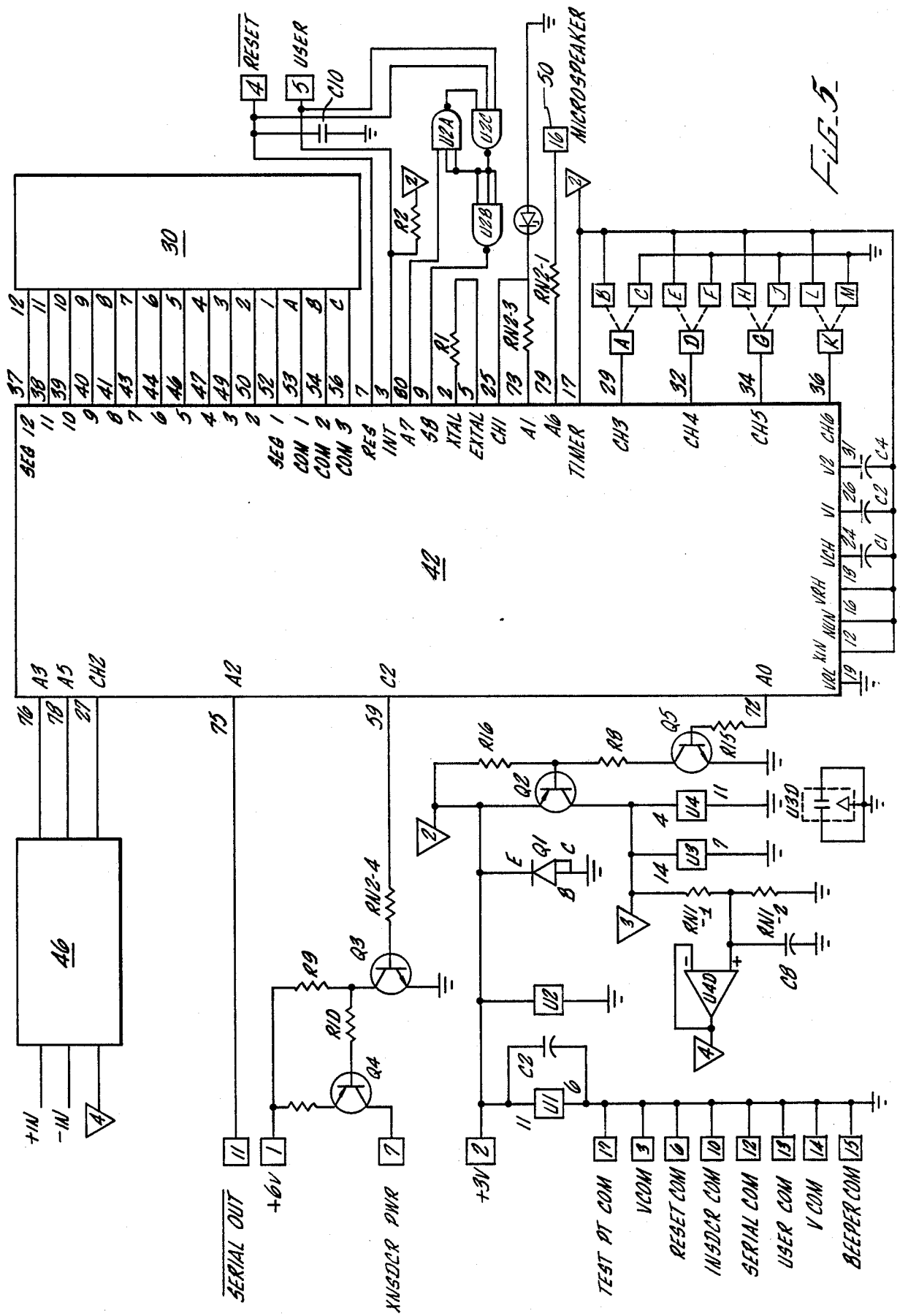
FIG. 5 is a system diagram.

FIG. 5 shows a detailed system block diagram which consists of a three-stage high-gain amplifier 46 with its associated baseline reference nulling circuit, a microprocessor 42 and a display 30. Components C1, C2, C4, C8 and C10 are capacitors; components R1, R2, RN1-1, RN1-2, RN2-1, RN2-3, RN2-4, R9, R10, R15 and R16 are resistors; components Q2, Q3, Q4 and Q5 are transistors; component U4D is an operational amplifier; components U2A, U2B and U2C are NAND gates and component 50 is a microspeaker. The strain gauge 36 (FIG. 4) is used to convert the intraocular pressure of the eye to an electrical impulse. When the contact head 28 of the transducer housing 26 is put in contact with the surface of the eye, then the central post 34 of the strain gauge 36 is caused to move which in turn causes the plate 35 on which the strain gauges are mounted to bend slightly. That in turn causes the resistance of the strain gauges 39 to increase/decrease. The strain gauge forms two of the resistive elements of a Wheatstone bridge. The output of the Wheatstone bridge is connected to the three-stage high-gain amplifier 46 where the signal is amplified for input to the microprocessor 42. The microprocessor then follows the sequence shown in the flow chart of FIGS. 10A through 10C to perform the analysis on the waveform from the three-stage high-gain amplifier 46. In that analysis, shown in the flow chart of FIGS. 10A through 10C, the dc component offset or baseline must be subtracted from the pressure waveform, shown in FIG. 8, to determine the relative differential signal of interest.

As shown in FIGS. 10A, 10B and 10C the analysis is as follows. A baseline search is initiated and then the baseline is tracked. If the change is positive, then the system tracks the rising edge. The slope of the rising edge is tracked until there is either no change or the change is negative. If there are consecutive samples in which there is no change, then a pressure reading is computed and the system then looks for a falling edge. If the slope is negative and the slope is greater than or equal to 5, then the system searches for the pressure and computes it. After the pressure reading is computed, the system analyzes for a falling edge as shown in FIG. 10B. The system then searches for a baseline. If no baseline is found, then the system exits the routine. If a baseline is found, then the baseline is tracked for a falling edge. If the sample change is negative, then the routine is exited. If there is no change, then the average of the last eight samples is computed and the system returns to the block in which the baseline is tracked for a falling edge. If the sample change is positive, then the system tracks the rising edge until there is no change or the change is negative. If there are three consecutive "no change" readings, then the pressure reading is computed and the routine is exited. If the sample change is negative and the slope is less than or equal to 5, then the routine is exited. If the slope is greater than or equal to 5, then there is a pressure search for a falling edge. If there are greater than ten samples in this search, then the routine is exited. If there are less than ten samples, then the pressure search for the falling edge is repeated until the pressure is found at which time the pressure is computed. After the pressure reading is computed, the routine is exited.

Referring to FIG. 7, which is a circuit of the three-stage high-gain amplifier 46 with its associated baseline reference nulling circuit, state 1 of the microprocessor logic involves finding a stable amplifier baseline to reference and calculate the relative amplitude of the pressure waveform shown in FIG. 8. To accomplish this, the micropressure applies an active high (capacitor discharge) signal from lead 78 to control lines 54 and 56 of the analog switches 58 and 60 for a period of 60 mS. This nulls both the second stage 62 and the third stage 64 of the amplifier circuitry by equalizing the charge on both sides of capacitors 66 and 68. The charge of the capacitors are neutralized because there is a 1.5 volt reference voltage supplied on lead 71 which equals the reference voltage of the second stage amplifier and is applied on the second-stage amplifier side of capacitor 66. Similarly, a 0.4 volt, set by resistors 72 and 74, is directly applied to the third-stage side of the capacitor 68 which equals this stage's reference voltage. This neutralizing effect equalizes both differential inputs for each amplifier stage resulting in a gain of zero, and removing any carrier signal. After 60 milliseconds, the capacitor discharge signal on leads 54 and 56 is terminated, which opens both of the analog switches 58 and 60 controlled by the microprocessor 42. During the 60 millisecond time period the microprocessor is processing data already received. Microprocessor 42, shown in FIG. 7, is also shown as microprocessor 42 in FIG. 5.

This design is unique because the microprocessor is able to use the capacitor discharge control to reach the baseline when needed, while dynamically processing the pressure waveform data. The amplifiers 62 and 64 are effectively dc coupled (since there is virtually an infinite time constant) which gives the microprocessor 42 a dc level signal to process. In a conventional ac coupled amplifier circuit, nulling would have to be accomplished either by complex precision auto-nulling hardware circuit or by operator manual calibration before instrument use.

When the activation switch has not been depressed for twenty seconds, the microprocessor 42 and transducer elements are turned off in order to conserve power and preserve the battery life. A small discrete circuit performs this function and also responds to depression of the activation button by activating the electronic elements and the transducer.

All elements of the tonometer instrument are connected to a multilayered circuit board. Mounted off the circuit board are four silver oxide batteries. Mounted on the circuit board 44 are the microprocessor, the microspeaker, and the discrete circuitry related to "wake-up" and transducer signal processing. Also on the circuit board are connectors to the display 30, the activation button 24, and the RS232 computer interface connector 32.

While the preferred embodiment of the system of the present invention has been illustrated and described, certain modifications and alternatives will be apparent to those skilled in the art and the present disclosure is intended to include such modifications and alternatives within the scope of the appended claims.

What is claimed is:

1. A baseline nulling system in which inputs to amplifier stages are dynamically equalized prior to and during signal analysis comprising amplifier means with a plurality of amplifier stages wherein a first stage is capacitively coupled to a second stage and said second stage is capacitively coupled to a third stage, analysis means connected to said third stage for receiving electronic signals from said third stage, corresponding to pressure measurements, analog switch means comprising a first analog switch and a second analog switch, said first analog switch being connected to said analysis means and to said second stage, and said second analog switch being connected to said analysis means and said third stage, and wherein said analysis means causes said first and second switches to open and close for a pre-determined period of time between the open state and closed state prior to said analysis means receiving electronic signals from said third stage and wherein said analog switch means causes the gain of said second and third stages to have a pre-determined gain when said first and second analog switches are open.

2. A system as in claim 1 wherein,
said predetermined gain in zero.

3. A system as in claim 1 including,
a display means is connected to said analysis means and is adapted to receive electronic signals corresponding to said pressure measurements and to digitally display numbers corresponding to said pressure measurements.

4. A system as in claim 3 wherein,
an electrical bridge is connected to said amplifier means and supplies said amplifier means with electronic signals corresponding to pressure measurements, and transducer means connected to said electrical bridge for supplying said bridge with electronic signals corresponding to said pressure measurements.

* * * * *